United States Patent [19]

Hamilton

[11] 4,072,059
[45] Feb. 7, 1978

[54] GRAIN PROBE

[75] Inventor: James T. Hamilton, Decatur, Ill.

[73] Assignee: Jaham Mfg. Co., Inc., Warrensburg, Ill.

[21] Appl. No.: 767,540

[22] Filed: Feb. 10, 1977

[51] Int. Cl.² .............................................. G01N 1/14
[52] U.S. Cl. .................................. 73/423 R; 73/425.2
[58] Field of Search .............................. 73/423, 425.2

[56] References Cited

U.S. PATENT DOCUMENTS

| 840,943 | 1/1907 | Ingold | 73/423 |
|---|---|---|---|
| 3,192,773 | 7/1965 | Wilson | 73/425.2 |
| 3,789,671 | 10/1971 | Larson | 73/423 |
| 4,037,476 | 7/1977 | McCrabb | 73/423 |

Primary Examiner—Herbert Goldstein
Attorney, Agent, or Firm—Emrich, Root, O'Keeffe & Lee

[57] ABSTRACT

A grain sampling probe device for insertion into grains comprises an elongated grain probe element which contains a plurality of openings extending along its length and a plurality of retaining brackets extending outwardly to define a passageway. Mounted integral to the grain probe is a hydraulic cylinder which is attached to a gate member, having a plurality of openings therein, which is slidably positioned within the passageway between the retaining brackets and the probe. The hydraulic cylinder selectively moves the gate member between an open position wherein the grain passes through the plurality of openings into the grain probe and a closed position wherein the openings are closed and the grain is sealed within the probe. A suction device is attached to the end of the probe to remove the collected grain after each sampling operation is completed.

7 Claims, 9 Drawing Figures

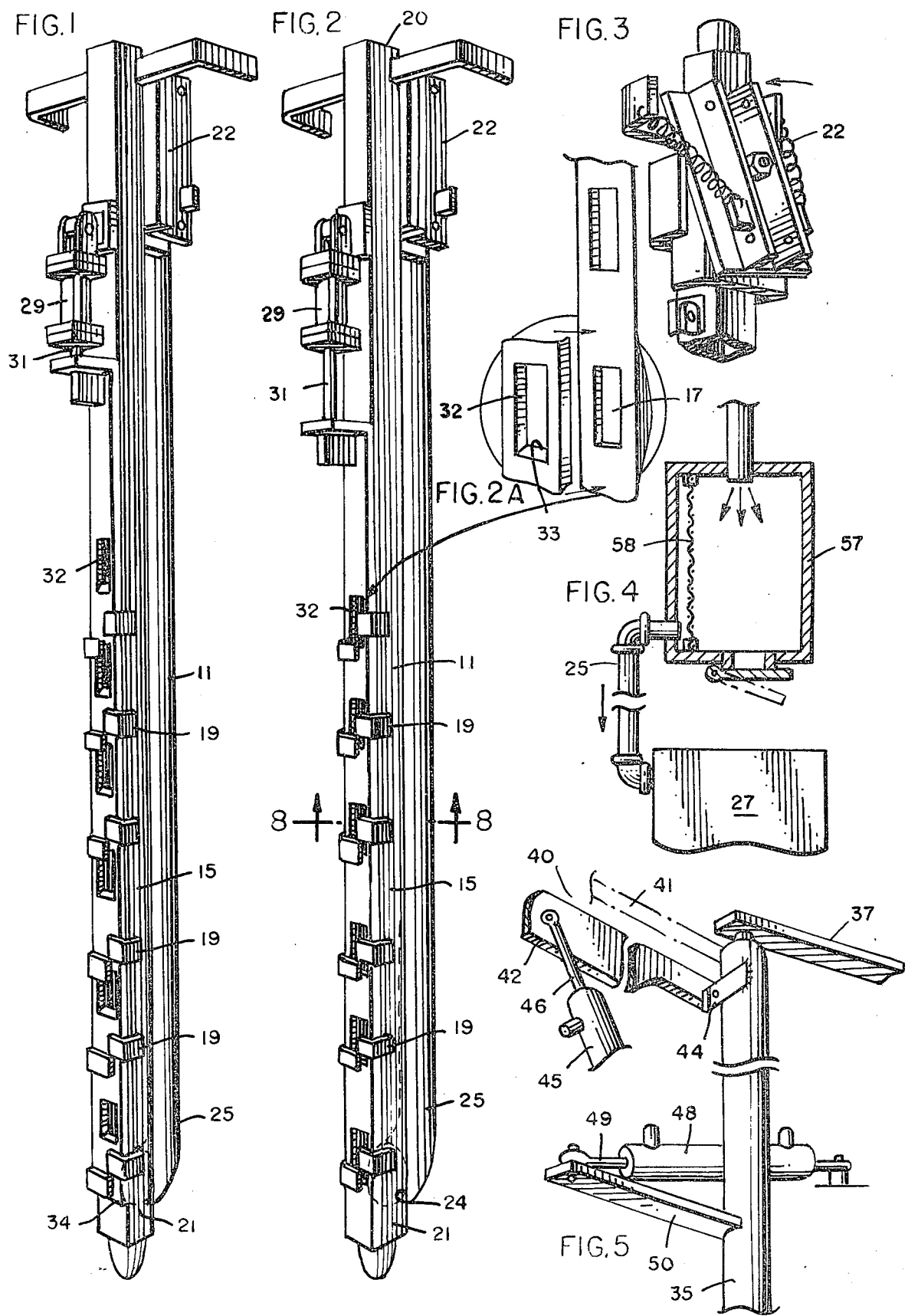

GRAIN PROBE

BACKGROUND OF THE INVENTION

This invention relates generally to a grain sampling probe device and more particularly to an improved grain sampling probe device having suction means engageable with the extended probe end to withdraw the collected grain from within the probe.

In the past, manual grain sampling devices have been generally constructed to comprise a tubular outer shell member and a tubular inner shell member positioned within the outer shell. Both the outer shell and the inner tube members include vertically spaced openings therein which may be selectively rotated and aligned together so that the vertical spaced openings are open to permit grain, such as corn, soybeans, wheat and the like, to be drawn into the grain probe. Upon the closure of the spaced openings, the sampling probe is then manually removed from the grain and the grain is manually collected from the probe for subsequent testing, as is well known in the art. The hand operated grain probe necessarily requires that the user thereof manually insert the probe into the grain material, and the failures of the user thereof to properly position the probe into the confined grain have resulted in improper and faulty grain measurement data. In an attempt to correct the deficiencies of such prior art devices, mechanical grain sampling probes have been designed which include inner and outer tubular members which are mechanically positioned over the confined grain and then automatically positioned downwardly such that the probe extends into the confined grain. The probe is then rotated such that the aligned holes permit the grain to fill the probe and then the probe is closed and withdrawn from the confined grain. Upon withdrawal of the probe, suction means, attached to the upper end of the probe, have been utilized to withdraw the grain collected within the probe to a sampling box which is located remote from the probe. However, it has been found that such devices often become clogged because of the high moisture content of the sampled grain. Additionally, because of the extended length of the probe and the weight of the grain therein, it has been difficult to utilize sufficient suction means to remove the grain from within the probe to a remote located sampling box and to maintain the probe free of sampled grain. Thus, these mechanical operated grain sampling probes have enjoyed only limited commercial acceptance.

SUMMARY OF THE INVENTION

It is one object of the present invention to provide an improved remote controlled grain sampling probe for collecting grain samples.

It is another object of the present invention to provide a grain sampling probe having suction means attached to the extended probe end to withdraw the collected grain sample from within the elongated probe member to a remote sampling box.

It is a further object of the present invention to provice a grain sampling probe having a structure which greatly reduces the suction force required in removing the collected grain sample from within the elongated probe member.

It is still a further object of the present invention to provide an improved grain sampling probe device utilizing relatively few parts, which is of simple construction and reliable in operation.

In the preferred embodiment of the present invention, the grain sampling probe device includes an elongated grain probe member having a plurality of vertically spaced openings extending along the length thereof and a plurality of retaining brackets extending outwardly therefrom which define a passageway therebetween. The upper end of the elongated grain probe member includes a bracket mounting which is pivotally connected to the frame member of the grain sampling device for positioning the probe member at predetermined locations with respect to the confined grain to be sampled. The lower probe end of the elongated probe member includes an opening therein which is connected by a conduit tube to a suction device which removes the collected sample of grain from within the probe. Mounted integral on the grain probe member adjacent the upper end thereof is a hydraulic cylinder which is attached to a gate member having a plurality of vertical openings therein which is slidably positioned within the passageway and held tightly against the elongated grain probe member by the retaining brackets. The hydraulic cylinder moves the gate member from a closed position wherein the plurality of vertical spaced openings in the probe member are covered by the gate member to an open position wherein the vertical openings in the gate member coincide and overlap the vertical openings in the probe member to permit the grain material to be collected within the probe member.

The elongated grain probe member is, preferably, mounted to the frame member which includes a vertical extending support pole which is adapted to be received by an upper support arm which is rigidly mounted to a support structure, as desired. The support pole is permitted to pivot about an axis to permit positioning of the grain probe in predetermined locations, as will hereinafter be described. Attached to the upper end of the support pole is a support arm member extending outwardly therefrom. The support arm member is engageable with one end of a first cylinder means with the opposite end of the cylinder means engaging the support pole. The operation of the first cylinder means rises and lowers the support arm in an upward and a downward plane. A second cylinder means is mounted to the supporting structure and engageable with a winged extension mounted to the support pole such that the operation of the second cylinder means rotates the support pole in a back and forth horizontal movement. The outer end of the support arm member, opposite the end attached to the support pole, is connected to the bracket mounting attached to the upper end of the elongated grain probe member. Thus, movement of the support arm member moves the elongated probe member up and down as desired. Additionally, a remote control device is utilized in controlling the first and second cylinder means and the hydraulic cylinder which is mounted on the grain probe member and engageable with the gate member. The remote control device further includes means for controlling the suction device connected by the conduit tube to the lower end of the elongated grain probe to withdraw the collected grain sample from the probe to a remote receiving chamber after each sampling operation.

In operation, the elongated grain probe is first positioned over the confined grain to be sampled. The control device then energizes the first hydraulic cylinder to move the support arm downwardly thereby lowering the grain probe into the confined grain. When the grain probe has been lowered into the body of the grain, the hydraulic cylinder mounted on the elongated grain probe and attached to the gate member is energized thereby moving the gate member from the closed position to the open position wherein the vertical openings in the gate member coincide and overlap the vertical openings in the elongated probe member to permit the grain material to be collected within the probe member. After the grain material has filled the probe member, the hydraulic cylinder is again actuated and moved from an open to the closed position wherein the gate member covers the vertical openings in the elongated probe member to close the same. The first hydraulic cylinder is then actuated and energized to move from a closed position to an open position to thereby raise upwardly the elongated grain probe member out of the confined grain. When the grain probe member is in the upper position, the suction device is energized and the grain is withdrawn from the elongated probe member through the conduit tube to a remote receiving chamber to thereby permit test measurements and data to be completed on the sampled grain. If it is desired to collect more than one test sample from the confined grain, the second hydraulic cylinder is energized and the support pole is horizontally rotated and the grain probe member is predeterminedly positioned over another area of the confined grain.

The unique grain sampling probe in accordance with the present invention provides a structure wherein the suction device is engageable with the end of the grain probe to withdraw the collected grain from within the probe. Because the suction device is primarily pulling downwardly upon the grain to remove the same from the probe, it has been found that clogging of the grain probe has been eliminated and that a greatly reduced suction force is required in removing the confined grain material from within the probe, a result which has heretofore been unattainable by the prior art.

BRIEF DESCRIPTION OF THE DRAWINGS

FIG. 1 is a side elevational view of the grain sampling probe in accordance with the present invention showing the hydraulic actuated gate member in the closed position;

FIG. 2 is a side elevational view of the sampling probe in accordance with the present invention showing the hydraulic actuated gate member in the open position;

FIG. 2A is an enlarged fragmentary view showing the vertical openings of the gate member coinciding and overlapping the vertical openings in the elongated grain probe member when in the open position;

FIG. 3 is a partial perspective view showing the bracket mounting device in accordance with the present invention;

FIG. 4 is an enlarged side elevational view showing the receiving chamber in accordance with the present invention;

FIG. 5 is an enlarged fragmentary view showing the frame mounting member in accordance with the present invention;

DETAILED DESCRIPTION OF THE DRAWINGS

Figure 6:
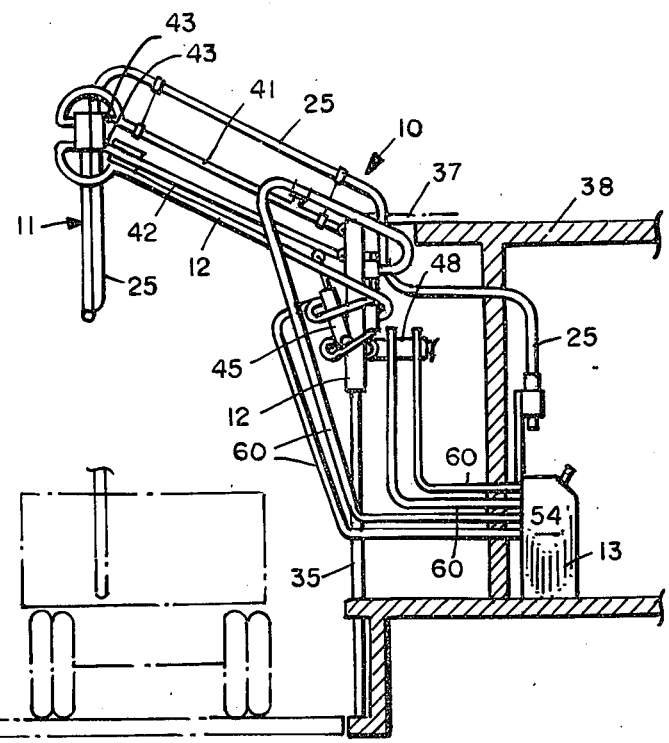
FIG. 6 is a perspective view showing the main sampling probe in accordance with the present invention.

Referring now to the drawings which illustrate the apparatus of the preferred embodiment of the present invention, the same reference numerals have been used throughout several figures to designate the same or similar components.

FIGS. 1 through 6 illustrate the construction of the grain sampling probe and its operation in practicing the preferred embodiment of the present invention. The grain sampling device 10 includes a grain probe portion 11, a probe mounting portion 12 and a control portion 13.

Figure 8:
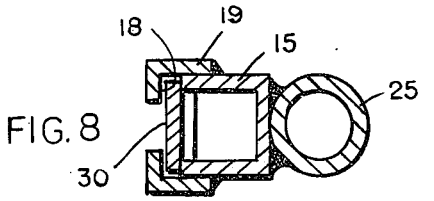
FIG. 8 is a section taken along lines 8—8 in FIG. 2.

The grain probe portion 11 is comprised of an elongated tubular grain probe member or element 15 having a plurality of vertically spaced openings 17 (FIG. 2A) extending along the length thereof and a plurality of L-shaped retaining brackets or means 19 extending outwardly from the elongated tubular probe member 15. The L-shaped brackets 19 define a passageway or channel 18 (FIG. 8) between the brackets and the elongated tubular probe member 15. The open upper end 20 of the elongated tubular grain probe member 15 includes a bracket mounting element 22 attached integral thereto and which is pivotally connected to the probe mounting portion 12 of the grain sampling device 10 for positioning the probe member 15 at predetermined locations with respect to the confined grain to be sampled. The lower probe end 21 of the elongated tubular probe member 15 includes an opening 24 therein which is operatively connected by a conduit tube 25 to a suction device or means 27 (FIG. 4) which removes the collected sample of grain from within the probe, as will hereinafter be described. Preferably, the lower probe end 21 rounded or conical in shape to reduce the friction of the grain material upon the probe as it is lowered into the grain material.

Mounted integral to the tubular probe member 15 and adjacent the upper end 20 thereof is a hydraulic cylinder 29 having a piston element 31 which is operatively connected to a gate member 30 having a plurality of vertical openings 32 (FIGS. 1, 2 and 2A) therein which is slidably positioned within the passageway 18 and retained against the elongated grain probe member by the L-shaped retaining brackets 19. When the hydraulic cylinder 29 is energized, the gate member is moved from a closed position (FIG. 1) wherein the plurality of vertical spaced openings 17 in the tubular probe member 15 are covered by the gate member 30 to an open position (FIG. 2) wherein the vertical spaced openings 32 in the gate member coincide and overlap the vertical spaced openings 17 in the tubular probe member 15 to permit the grain material to be collected within the probe member. Preferably, the spaced openings 32 in the gate member 30 are beveled inwardly to provide a sharp cutting surface edge 33 (FIG. 2A) so that upon the movement of the gate member between the open and closed position, the cutting edge prevents grain material from clogging and preventing the movement of the gate member from the open to the closed position.

The elongated tubular grain probe member 15 is, preferably, operatively connected to a probe mounting portion 12 which includes a vertical extending frame or support pole 35 which is adapted to be received by an upper support arm 37 which is rigidly mounted to a support structure 38 (FIG. 6), as desired. The upper end 36 (FIG. 5) of support pole 35 is engageable with the upper support arm 37 to permit the support pole to pivot about an axis to permit positioning of the grain probe in predetermined locations, as will hereinafter be described. Attached to the upper end 36 of the support pole is a support arm member means 40 extending outwardly therefrom. The support arm member means 40 includes upper and lower holding bars 41 and 42 (FIG. 5) respectively. The lower holding bar 42 of the support arm member means 40 is operatively connected with a piston element 46 of a first cylinder member or means 45 with the cylinder means 45 being anchored to the support pole 35 (FIG. 6). Actuation of the first cylinder means 45 causes the piston element to move outwardly to thereby raise the lower holding bar 42 and the corresponding support arm means 40 in an upward and a downward plane. A second cylinder member or means 48 is mounted to the supporting structure and includes a piston element 49 operatively engageable with a winged extension 50 mounted to the support pole 35. Actuation of the second cylinder means 48 moves the piston element 49 to thereby rotate the support pole 35 in a back and forth horizontal movement to thereby position the grain probe member 15 in predetermined location in the confined grain.

The outer ends 43 (FIG. 6) of the support arm member means 40, opposite the ends 44 (FIG. 5) attached to the support pole 35, are connected to the bracket mounting element 22, attached to the upper end 20 of the elongated grain probe member 15, as is well known in the art. Thus, movement of the support arm member means 40 moves the elongated tubular probe member 15 up and down while maintaining the same in substantially a vertical position, as desired.

Figure 7:
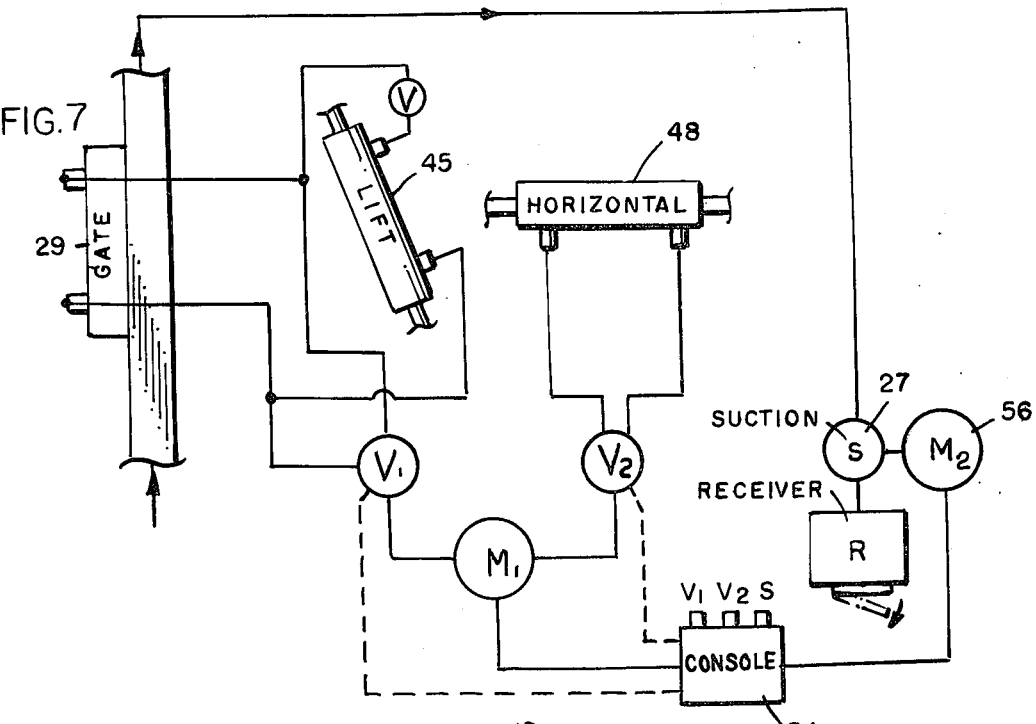
FIG. 7 is a schematic drawing of the control mechanism for operation the grain sampling probe in accordance with the present invention.

Additionally, a remote control housing device 54 is utilized in controlling the first and second cylinder means and the hydraulic cylinder 29, mounted on the tubular probe member 15, and engageable with the gate member 30. The remote control housing device includes actuator means 56 (FIG. 7) operatively connected to the suction device or means 27 (FIG. 4), which is operatively connected through a screen element 58 to the remote receiving chamber or means 57 by conduit tube 25 to the lower end 21 of the tubular probe 15 to withdraw the collected grain sample from the probe to the remote receiving chamber 57 after each sampling operation. The remote control device further includes fluid conduit means 60 operatively connected to the first and second cylinder means 45 and 48 to actuate the same to position the grain probe as hereinabove described.

In operation, the elongated tubular grain probe 15 is positioned over the confined grain to be sampled. The remote control means 54 then actuates the first cylinder means 45 to thereby move the support arm member means 40 downwardly thereby lowering the tubular grain probe 15 into the confined grain. When the grain probe has been lowered into the body of the grain material, the hydraulic cylinder 29, mounted on the elongated tubular grain probe 15 and attached to the gate member 30 from the closed position to the open position wherein the vertical spaced openings 32 in the gate member 30 coincide and overlap the vertical spaced openings 17 in the elongated probe member 15 to permit the grain material to be collected within the probe member. After the grain material has filled the tubular probe member 15, the hydraulic cylinder 29 is again actuated to move the gate member from open to the closed position wherein the gate member covers the vertical spaced openings 17 in the elongated tubular probe member 15 to close the same. The first cylinder means 48 is then actuated and energized to move the piston element 46 from a closed position to an open position to thereby raise upwardly the support arm member means 40 and the attached probe member 15 out of the confined grain. When the tubular probe member 15 is in the upper position, the control device 54 energized the actuator means to operate the suction device 27 to withdraw the grain from the elongated tubular probe member 15 through the conduit tube 25 to the remote receiving chamber 51 to thereby permit test measurements and data to be completed on the sampled grain. If it is desired to collect more than one test sample from the confined grain, the second cylinder means 48 is actuated and the support pole 35 is horizontally rotated and the grain probe member is predeterminedly positioned over another area of the confined grain and the sampling procedure may be repeated.

The unique grain sampling probe in accordance with the present invention provides a structure wherein the suction device is engageable with the end of the grain probe to withdraw the collected grain from within the probe. Additionally, it has been found that if the end 34 of the gate member 30 does not completely cover the last vertical spaced opening 17 when the gate member 30 is in the closed position, then the suction acts upon the grain material within the tubular prove at a much faster rate than if the last vertical spaced opening is completely sealed. Also, because the suction device is primarily pulling downwardly upon the grain to remove the same from the probe, it has been found that clogging of the grain probe has been eliminated and that a greatly reduced suction force is required in removing the confined grain material from within the probe, a result which had heretofore been unattainable by the prior art.

I claim:
1. A sampling device for insertion into a body of confined grain, including in combination:
   a tubular probe member having a closed lower end with an opening therein and a plurality of vertical spaced openings extending the length thereof,
   gate means having a plurality of sectional spaced openings therein, said gate means being engageable with said tubular probe member and movable from a closed position wherein said gate means substantially closes said plurality of vertical spaced openings in said probe member to an open position wherein said vertical openings on said gate means are in alignment with said vertical spaced opening on said tubular probe member,
   bracket means mounted on the end of said tubular probe member opposite the closed lower end,
   probe mounting means attached to said bracket means to hold said tubular probe member in substantially a vertical position,
   suction means operatively connected to said opening on said closed lower end of said probe member, and
   control means for operating said probe mounting means in positioning said probe member in the body of the confined grain, said control means further moving said gate means between a closed and an open position to permit grain to fill said tubular probe member and actuating said suction means to withdraw the collected grain from said probe when the same has been withdrawn from the body of the confined grain.

2. The sampling device in accordance with claim 1 wherein said tubular probe member includes a plurality of retainer brackets mounted thereon which define a passageway between said brackets and said probe member, said passageway being adapted to receive and retain said gate means against said tubular probe member.

3. The sampling device in accordance with claim 1 wherein said control means includes cylinder means mounted on said tubular member and engageable with said gate means to move the same between said open and said closed positions.

4. The sampling device in accordance with claim 1 wherein said probe mounting means includes a support pole having support member means extending outwardly therefrom and attached to said bracket means on said tubular probe member.

5. The sampling device in accordance with claim 4 wherein said probe mounting means further includes first cylinder means engageable with said support member means and operable between an extended and closed position to raise and lower said tubular probe member.

6. The sampling device in accordance with claim 1 wherein said suction means includes a receiving chamber operatively connected to a conduit tube attached to said opening to receive the collected grain withdrawn from said tubular probe member.

7. A probe mechanism for use with a grain sampling device having a probe member mounting frame adapted to hold and position the probe mechanism in substantially a vertical position, control means for operating the probe member mounting frame in positioning the probe mechanism and suction means for removing the sampled grain from the probe mechanism, and probe mechanism including in combination:

a tubular probe means having a closed lower end with an opening therein and a plurality of vertical spaced openings extending the length thereof, bracket means mounted on the end of said tubular probe member opposite the closed lower end, and gate means having a plurality of sectional spaced openings therein, said gate means being engageable with said tubular probe member and movable from a closed position wherein said gate means substantially closes said plurality of vertical spaced openings in said probe member to an open position wherein said vertical openings on said gate means are in alignment with said vertical spaced opening on said tubular probe member, with the suction means being operatively connected to said opening on said closed lower end of said probe to thereby remove the collected grain.

* * * * *